United States Patent [19]
Park et al.

[11] Patent Number: 5,939,093
[45] Date of Patent: Aug. 17, 1999

[54] COSMETIC PACK IN THE FORM OF A SHEET

[75] Inventors: Jong-Jin Park, Kyunggi-do; Jae-Whan Kim, Seoul; Oh-Seung Kwon, Kyunggi-do, all of Rep. of Korea

[73] Assignee: Hansol Paper Co., Ltd. and Hansol Patech Co., Ltd., Rep. of Korea

[21] Appl. No.: 09/119,960

[22] Filed: Jul. 21, 1998

[30] Foreign Application Priority Data

Jun. 17, 1998 [KR] Rep. of Korea ................ 98-22811

[51] Int. Cl.$^6$ ..................................................... A61K 7/00
[52] U.S. Cl. ........................ 424/443; 424/444; 424/445; 424/401; 424/78.03
[58] Field of Search .................................. 424/443, 444, 424/445, 401, 78.03

[56] References Cited

FOREIGN PATENT DOCUMENTS

0750905 A2  2/1997  European Pat. Off. .

*Primary Examiner*—Cecilia J. Tsang
*Assistant Examiner*—C. Delacroix-Muirheid
*Attorney, Agent, or Firm*—Finnegan, Henderson, Farabow, Garrett & Dunner, L.L.P.

[57] ABSTRACT

This invention relates to a sheet-type cosmetic pack, wherein a cosmetic composition layer comprising a cation-based water-soluble copolymer expressed by the following formula 1 and a partially cross-linked water-soluble polymer is introduced between the protective film layer and the substrate layer supporting the cosmetic composition:

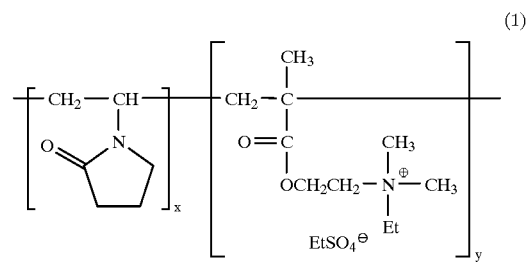

(1)

wherein, x is 0.6~0.8, y is 0.2~0.4, and x+y=1.

The sheet-type cosmetic pack of this invention has the following advantages in that a) the keratotic plugs can be effectively removed from the skin, b) maintenance of clean skin pores imparts flexibility to the skin of a nose, c) a shortened drying time prevents a residue of cosmetic substances in the skin after a peel-off, and d) pain is mitigated due to easy peel-off.

9 Claims, 1 Drawing Sheet

COSMETIC PACK IN THE FORM OF A SHEET

FIELD OF THE INVENTION

This invention relates to a sheet-type cosmetic pack, wherein a cosmetic composition layer comprising a cation-based water-soluble copolymer expressed by the following formula 1 and a partially cross-linked water-soluble polymer is introduced between the protective film layer and the substrate layer supporting the cosmetic composition:

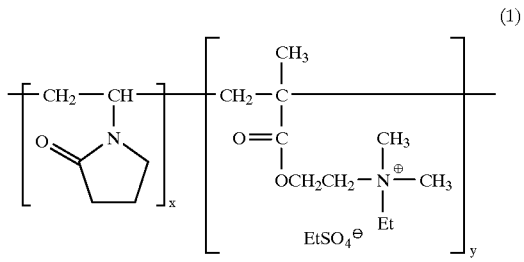

wherein, x is 0.6~0.8, y is 0.2~0.4, and x+y=1.

The sheet-type cosmetic pack of this invention has the following advantages in that a) the keratotic plugs can be effectively removed from the skin, b) maintenance of clean skin pores imparts flexibility to the skin of a nose, c) a shortened drying time prevents a residue of cosmetic substance in the skin after a peel-off, and d) pain is mitigated due to easy peel-off.

BACKGROUND OF THE INVENTION

Keratotic plugs are contaminants formed in the pores of skin, which have been keratinized with sebaceous matters and dirt. If a proper treatment is not taken, various skin diseases may result therefrom. Such keratotic plugs cannot be easily removed even after cleansing. In fact, the ordinary facial detergent cannot sufficiently remove the keratins deep inside the pores of the skin. Thus, there remains a need for a convenient sheet-type cosmetic pack which can effectively remove the excessive secretion of sebaceous matters and dirt from the pores of the skill.

Among the conventional methods to remove keratotic plugs from the skin, a variety of methods has been proposed in such a manner to enhance the strength of a film derived from the cosmetic composition layer at the time of a peel-off. For example, there is a method of obtaining a sheet-type pack by spreading a gel made of polyacrylic acid and cross-linking agent on a non-woven fabric as disclosed in Japanese Patent Laid-Open No. 58-180408. Also, there is a sheet-type pack made of alginic acid, a water-soluble polymer and a cross-linking agent as disclosed in Japanese Patent Laid-Open No. 2-145505.

To effectively remove keratotic plugs formed in the pores of the skin, there is a method of obtaining a sheet-type pack by incorporating various base forms of polymers into a water-soluble polymer containing a layer of cosmetic composition. The examples include cationic, anionic and ampho-teric groups such as carboxyl, sulfonic acid group, amino group and ammonium group, as disclosed in Japanese Patent Laid-Open No. 5-97627. This method has been proven to be effective in removing keratotic plugs but still has a drawback such as a slow drying of the cosmetic composition layer.

SUMMARY OF THE INVENTION

The objective of this invention is to provide a non-irritant sheet-type cosmetic pack, wherein a cation-based water-soluble copolymer, so obtained from copolymerization of vinylpyrrolidone and N,N-dimethylaminoethylmethacrylic acid sulfate, is added to the cosmetic composition for the purpose of resolving the miscible problems associated with the conventional process of mixing various polymers containing base into a water-soluble polymer and effectively removing the keratotic plugs. At the same time, the strength of a film of the cosmetic composition layer is enhanced by means of a partial cross-linkage of a water-soluble polymer in the presence of a cross-linking agent. In conjunction, the enhancement of adsorptive power following the use of silica powder may effectively remove the keratotic plugs, and the residue thereof is non-existent after the peel-off. Finally, the removal of dirt from the pores of the skin imparts flexibility to the skin, and the easy peeling from the skin prevents pain therefrom.

Figure 1:
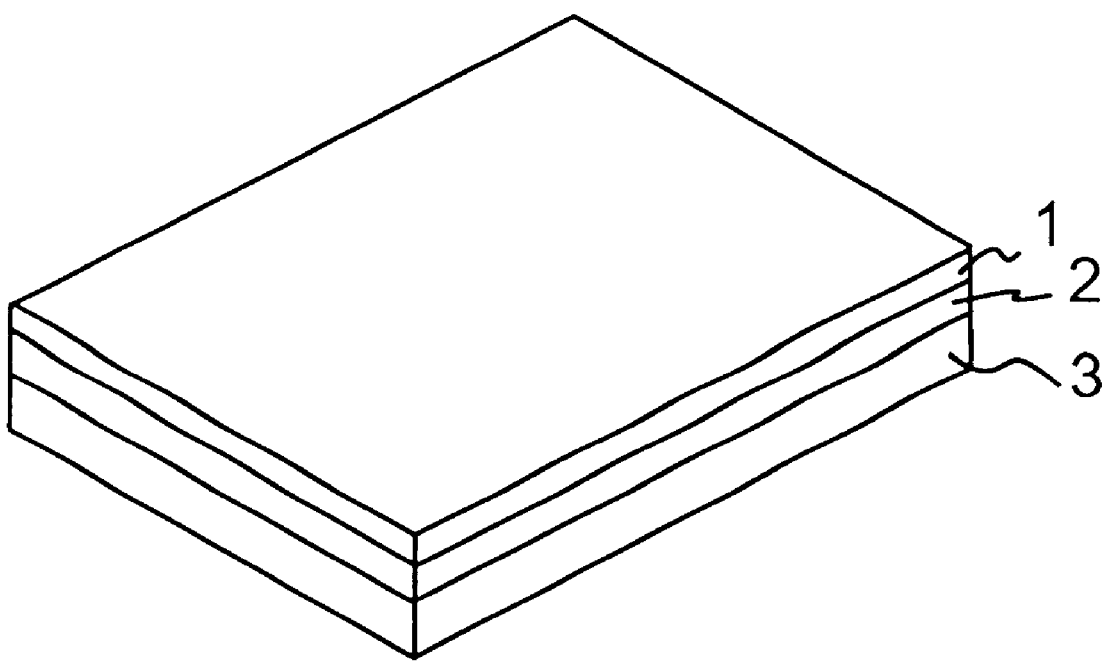
FIG. 1 is a cross-sectional view schematics illustrating the sheet-type cosmetic pack according to this invention.

(Description of main codes in the drawings)
1: Protective film layer
2: Cosmetic composition layer
3: Substrate layer

DETAILED DESCRIPTION OF PREFERRED EMBODIMENTS

This invention is characterized by a sheet-type cosmetic pack comprising a protective film layer which is peeled off before use, a cosmetic composition layer containing the cosmetic raw material composition, and a substrate layer supporting the cosmetic composition, wherein said cosmetic raw material composition layer contains a water-soluble polymer which is partially cross-linked by a cross-linking agent and a cationic copolymer expressed by the following formula 1:

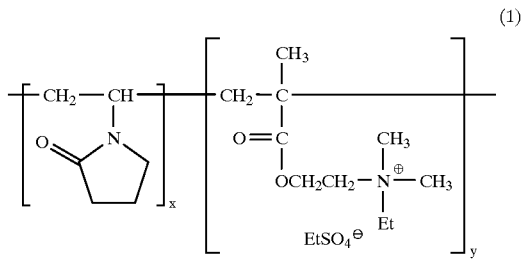

wherein, x is 0.6~0.8, y is 0.2~0.4, and x+y=1.

This invention is explained in more detail as set forth hereunder:

The accompanying FIG. 1 is a cross sectional view schematics illustrating a sheet-type cosmetic pack according to this invention. The sheet-type cosmetic pack comprises three layers: a protective film layer which is peeled off before use, a cosmetic composition layer containing the cosmetic raw material composition, and a substrate layer supporting the cosmetic composition.

For the effective removal off the keratotic plugs, the cation-based water-soluble copolymer expressed by the above formula 1 is incorporated into the cosmetic composition layer of this invention as a film-forming agent. Meanwhile the interpenetrating polymer network is established by means of it partial cross-linking reaction of a water-soluble polymer in order to ensure the complete removal of the cosmetic residue in the skin after peeling and the mitigation of pain due to easy peeling-off.

The cation-based water-soluble copolymer expressed by the above formula 1 for removing keratotic plugs is a copolymer obtained by copolymerization of a vinylpyrrolidone monomer, having in excellent film-forming capacity, adsorptive power and water solubility, and N,N-dimethylaminoethylmethacrylic acid sulfate having excellent viscosity retention and fat adsorptive power. The compatibility of these homopolymers such as polyvinylpyrrolidone or poly-N,N-dimethylaminoethylmethacrylic acid sulfate decreases due to the limited solubility with respect to the cosmetic composition. On the other hand, the copolymer of the present invention has a broad compatibility due to the fact that each molecule simultaneously retains two essential characteristics. In particular, the copolymer herein call effectively remove keratotic plugs by suppressing an increase in viscosity, which in turn stabilizes the coating property of the composition and provides a homogeneous miscible property. As for the cation-based water-soluble copolymer expressed by the formula 1, it is preferable that the amount thereof be in the range of 10~25 wt % of the total composition of the cosmetic raw material composition. If the amount is less than 10 wt %, the stability of the composition is lowered due to the decrease in the removal rate of the keratotic plugs. However, if it exceeds 25 wt %, the composition may encounter such problems as an increase in viscosity and poor miscible property.

In order to enhance the strength of the film at the time of peeling-off of the sheet-type cosmetic pack, the water-soluble polymers are added therein. From such water-soluble polymers by means of a cross-link agent, the film in the cosmetic composition layer having a partial interpenetrating polymer network is established. By increasing the strength of the film, the sheet-type cosmetic pack can effectively remove the keratotic plugs, prevent pain due to an easier peeling-off, and maintain clean and healthy skin pores. Examples of a water-soluble polymer having a molecular weight in the range of 100,000~1,000,000 include hydroxypropyl cellulose, hydroxypropylmethylcellulose, polyvinylpyrrolidone, polyvinyl alcohol, gelatin, methylcellulose, polyacrylic acid, polyethylene oxide, ethylcellulose, and carboxylmethylcellulose. As for the water-soluble polymer, it is preferable that the amount thereof be in the range of 30~55 wt % to the total composition of the cosmetic raw material composition layer. If the amount is less than 30 wt %, the coating property within the substrate layer deteriorates. However, if it exceeds 55 wt %, the loss of adsorptive power to the keratotic plugs may occur during the peel-off.

In particular, for the achievement of a partial cross-linkage as one embodiment of this invention, it is preferable that the amount of the water-soluble polymer containing such cross-linkage functional groups as hydroxy group or carboxyl group be in the range of 3~20 wt % to the total composition of the water-soluble polymer. The partial cross-linkage according to this invention is determined by the remaining hydroxy or carboxyl groups after the condensation reaction of the hydroxy or carboxyl groups at the side chain of the water-soluble polymer and the cross-linking agent. Such partial cross-linkage may vary depending on the amount of the cross-linking agent, time, and temperature thereof. If the cross-linkage is negligible, the objective of this invention cannot be achieved due to the reduction of the film strength, but if the partial cross-linkage is excessive, the overly dry film fails to adhere to the skin of a nose.

Therefore, in order to achieve an embodiment of this invention for the partial cross-linkage, the cross-linking agent is incorporated into the total composition in the range of 2~7 wt %. Then, the cross-linking reaction is carried out at the temperature of 70–75° C. for 10~15 minutes. Through such reaction, a partial cross-linkage within the 20% range may be obtained, which is measurable by FT-IR or NMR. The cross-linking agent of this invention designed to perform the partial cross-linkage of the water-soluble polymers is selected from the group consisting of calcium chloride, aluminum sulfate, polyethylene glycol glysidyl ether, and triglycerine diglysidyl ether. The film formed from the cross-linking reaction contains water in the range of 5~15 wt % depending on the manufacturing condition.

Further, the cosmetic raw material composition layer may contain a variety of components in accordance with its use. e.g., cosmetic raw materials for moisture retention and absorption of sebum, adjunctive cosmetic raw materials for removal of keratotic plugs, silica-based absorbents, whitening agents, pigments, dyes, perfume, anti-inflammatory agents, viscosity enhancers, moisture-retention agents, surfactants, preservatives, bactericidal agents, and pores-reducing agents.

As for the cosmetic raw material for moisture retention, the available examples include ethylene glycol, diethylene glycol, triethylene glycol, polyethylene glycol, and glycerin. It is preferable that the amount thereof be in the range of 1~1.5 wt % to the total chemical composition of the cosmetic composition layer. As for the ingredient for pore reduction, the available examples include hamamelis, tannic acid, citric acid, sulfuric acid, zinc oxide, zinc sulfate, allantoin, and zinc carbonate sulfonic acid. It is preferable that the amount thereof be in the range of 1–2 wt % to the total chemical composition of the cosmetic composition layer. For fragrance, a perfume such as mint, lavender and jasmin are incorporated into the total chemical composition of the cosmetic composition layer in the range of 0.1~1 wt %. In addition, to ensure the effective removal of the keratotic plugs through better adsorption of the cosmetic composition and to impart flexibility to the skin after removal of the keratotic plugs and dirt from the skin without any residue of the cosmetic composition, the silica powder is incorporated into the total composition in the range of 1~3 wt %. In this case, for the effective dispersion of the water-soluble polymer and silica, a commonly available surfactant is incorporated into the total composition in the range of 0.7~1.5 wt %. If the amount of surfactant is less than 0.7 wt %, the ongoing phase separation of the cosmetic composition layer makes it difficult to effectively remove the keratotic plugs, but if it exceeds 1.5 wt %, a poor adhesiveness to the skin of a nose results, thereby preventing the effective removal of the keratotic plugs.

As described above, on top of the cosmetic raw material composition layer, there is a protective film layer which is peeled off before use, and in the bottom thereof, there is a substrate layer supporting the cosmetic composition. For the purposes of protecting the cosmetic composition layer, preventing drying and facilitating the peeling of the sheet-type cosmetic pack, the protective film layer component may include polyester, polypropylene, polyethylene, and nylon. Further, the available examples of the substrate layer component include cellulose fibers such as rayon and acetate, natural fibers such as cotton and wool, and synthetic fibers with excellent ventilation and moisture permeability properties such as vinyl chloride, polyester, acrylate, polyethylene and polypropylene. When the sheet-type cosmetic pack having a multi-layer structure as aforementioned is pressurized using a roller, the ingredients contained in the cosmetic raw material composition layer are laminated to the substrate layer. Thus, the successful coating of these substances to the substrate may contribute much to the excellent contour of the sheet-type cosmetic pack.

This invention is explained in more detail based on the following examples but is not limited thereby.

| Example 1 | |
|---|---|
| Cation-based water-soluble copolymer (formula 1: H · C polymer 3A. Osaka Organic Chem. Co. of Japan) | 20 wt % |
| Polyvinyl alcohol | 10 wt % |
| Polyethylene glycol glysidyl ether | 2 wt % |
| Carboxylmethyl cellulose | 10 wt % |
| Titanium oxide | 0.5 wt % |
| Silica (Aerosil 380) | 1 wt % |
| Glycerin | 1 wt % |
| Ethanol | 9 wt % |
| Surfactant (BYK 346) | 1 wt % |
| Distilled water | 45.5 wt % |

The cosmetic raw material substance with film-forming property was homogeneously stirred, and with the addition of distilled water, its viscosity was adjusted to 4,000 cps. The liquid phase material was incorporated into the peel-off polypropylene sheet in a thickness of 300 μm, using a bar-coater and dried under hot air at 75° C. for 10 minutes. Then, a non-woven fabric of thickness or 50 μm, which is a substrate having moisture permeability, was placed on top of the dried cosmetic material, and a roller was used for lamination. After the drying process, water remaining in the cosmetic composition layer was in the range of 5~15%.

| Example 2 | |
|---|---|
| Cation-based water-soluble copolymer (formula 1: H · C polymer 3A. Osaka Organic Chem. Co. of Japan) | 23 wt % |
| Polyethylene oxide | 5 wt % |
| Polyethylenecglycol glysidyl ether | 3 wt % |
| Carboxylmethyl cellulose | 10 wt % |
| Titanium oxide | 1 wt % |
| Silica (Aerosil 380) | 1 wt % |
| Ethylene glycol | 1 wt % |
| Ethanol | 10 wt % |
| Jasmin | 0.2 wt % |
| Distilled water | 45.8 wt % |

A sheet-type cosmetic pack was prepared in the same manner as in Example 1, using the cosmetic raw material substances with the film-forming property.

| Example 3 | |
|---|---|
| Cation-based water-soluble copolymer (formula 1: H · C polymer 5. Osaka Organic Chem. Co. of Japan) | 23 wt % |
| Polyethylene oxide | 10 wt % |
| Triglycerine diglysidyl ether | 2 wt % |
| Polyacrylic acid | 5 wt % |
| Titanium oxide | 1 wt % |
| Silica (Aerosil 380) | 1 wt % |
| Glycerin | 1 wt % |
| Ethanol | 10 wt % |
| Lavender oil | 0.5 wt % |
| Distilled water | 46.5 wt % |

A sheet-type cosmetic pack was prepared in the same manner as in Example 1, using the cosmetic raw material substances with the film-forming property.

| Example 4 | |
|---|---|
| Cation-based water-soluble copolymer (formula 1: H · C polymer INS, Osaka Organic Chem. Co. of Japan) | 10 wt % |
| Polyvinylpyrrolidone | 20 wt % |
| Polyvinyl alcohol | 10 wt % |
| Polyethylenecglycol glysidyl ether | 3 wt % |
| Polyacrylic acid | 3 wt % |
| Titanium oxide | 1 wt % |
| Silica (Aerosil R972) | 1 wt % |
| Polyethylene glycol | 1 wt % |
| Ethanol | 10 wt % |
| Hamamelis | 2 wt % |
| Distilled water | 39 wt % |

A sheet-type cosmetic pack was prepared in the same manner as in Example 1, using the cosmetic raw material substances with the film-forming property.

| Example 5 | |
|---|---|
| Cation-based water-soluble copolymer (formula 1: H · C polymer INP, Osaka Organic Chem. Co. of Japan) | 10 wt % |
| Polyvinylpyrrolidone | 23 wt % |
| Polyethyleneglycolglysidylether | 2 wt % |
| Polyacrylic acid | 5 wt % |
| Titanium oxide | 1 wt % |
| Silica (Syloid W 300) | 2 wt % |
| Glycerin | 1 wt % |
| Ethanol | 9 wt % |
| Surfactant (BYK-307) | 1 wt % |
| Mint perfume | 0.5 wt % |
| Distilled water | 45.5 wt % |

A sheet-type cosmetic pack was prepared in the same manner as in Example 1, using the cosmetic raw material substances with the film-forming property.

| Example 6 | |
|---|---|
| Cation-based water-soluble copolymer (formula 1: H · C polymer 2, Osaka Organic Chem. Co. of Japan) | 20 wt % |
| polyvinyl alcohol | 10 wt % |
| Polyvinylpyrrolidone | 10 wt % |
| Calcium chloride | 2 wt % |
| Polyacrylic acid | 5 wt % |
| Titanium oxide | 1 wt % |
| Silica (Syloid W 500) | 2 wt % |
| Glycerin | 1 wt % |
| Ethanol | 10 wt % |
| Distilled water | 39 wt % |

A sheet-type cosmetic pack was prepared in the same manner as in Example 1, using the cosmetic raw material substances with the film-forming property.

| Example 7 | |
|---|---|
| Cation-based water-soluble copolymer (formula 1: H · C polymer 2, Osaka Organic Chem. Co. of Japan) | 20 wt % |
| Hydroxypropylmethyl cellulose | 20 wt % |
| Aluminum sulfate | 3 wt % |
| Polyacrylic acid | 5 wt % |
| Titanium oxide | 1 wt % |
| Silica (Aerosil 150) | 1 wt % |
| Polyethyleneglycol | 2 wt % |
| Ethanol | 10 wt % |

Example 7

| | |
|---|---|
| Lavender oil | 0.5 wt % |
| Distilled water | 37.5 wt % |

A sheet-type cosmetic pack was prepared in the same manner as in Example 1, using the cosmetic raw material substances with the film-forming property.

Comparative example 1

| | |
|---|---|
| Cation-based water-soluble copolymer (formula 1: H · C polymer 3A, Osaka Organic Chem. Co. of Japan) | 20 wt % |
| Polyvinyl alcohol | 10 wt % |
| Carboxylmethylcellulose | 10 wt % |
| Titanium oxide | 0.5 wt % |
| Silica (Aerosil 380) | 1 wt % |
| Glycerin | 1 wt % |
| Ethanol | 9 wt % |
| Surfactant (BYK 346) | 1 wt % |
| Distilled water | 47.5 wt % |

A sheet-type cosmetic pack was prepared in the same manner as in Example 1, using the cosmetic raw material substances with the film-forming property.

Comparative example 2

| | |
|---|---|
| Cation-based water-soluble copolymer (formula 1: H · C polymer 3A, Osaka Organic Chem. Co. of Japan) | 23 wt % |
| Polyethylene oxide | 5 wt % |
| Carboxylmethyl cellulose | 10 wt % |
| Titanium oxide | 1 wt % |
| Silica (Aerosil 380) | 1 wt % |
| Ethylene glycol | 1 wt % |
| Ethanol | 10 wt % |
| Jasmin | 0.2 wt % |
| Distilled water | 48.8 wt % |

A sheet-type cosmetic pack was prepared in the same manner as in Example 1, using the cosmetic raw material substances with the film-forming property.

Comparative example 3

| | |
|---|---|
| Cation-based water-soluble copolymer (formula 1: H · C polymer 5, Osaka Organic Chem. Co. of Japan) | 23 wt % |
| Polyethylene oxide | 10 wt % |
| Polyacrylic acid | 5 wt % |
| Titanium oxide | 1 wt % |
| Silica (Aerosil 380) | 1 wt % |
| Glycerin | 1 wt % |
| Ethanol | 10 wt % |
| Lavender oil | 0.5 wt % |
| Distilled water | 48.5 wt % |

A sheet-type cosmetic pack was prepared in the same manner as in Example 1, using the cosmetic raw material substances with the film-forming property.

Comparative example 4

| | |
|---|---|
| Polyvinylpyrrolidone | 30 wt % |
| Polyvinyl alcohol | 10 wt % |
| Polyethyleneglycolglysidylether | 3 wt % |
| Polyacrylic acid | 3 wt % |
| Titanium oxide | 1 wt % |
| Silica (Aerosil R972) | 1 wt % |
| Polyethyleneglycol | 1 wt % |
| Ethanol | 10 wt % |
| Hamamelis | 2 wt % |
| Distilled water | 39 wt % |

A sheet-type cosmetic pack was prepared in the same manner as in Example 1, using the cosmetic raw material substances with the film-forming property.

Comparative example 5

| | |
|---|---|
| Polyvinylpyrrolidone | 33 wt % |
| Polyacrylic acid | 5 wt % |
| Titanium oxide | 1 wt % |
| Silica (Syloid W 300) | 2 wt % |
| Glycerin | 1 wt % |
| Ethanol | 9 wt % |
| Surfactant (BYK-307) | 1 wt % |
| Mint perfume | 0.5 wt % |
| Distilled water | 47.5 wt % |

A sheet-type cosmetic pack was prepared in the same manner as in Example 1, using the cosmetic raw material substances with the film-forming property.

Comparative example 6

| | |
|---|---|
| Cation-based water-soluble copolymer (formula 1:H · C polymer 2, Osaka Organic Chem. Co. of Japan) | 20 wt % |
| Polyvinyl alcohol | 10 wt % |
| Polyvinylpyrrolidone | 10 wt % |
| Polyacrylic acid | 5 wt % |
| Titanium oxide | 1 wt % |
| Silica (Syloid W 500) | 2 wt % |
| Glycerin | 1 wt % |
| Ethanol | 10 wt % |
| Distilled water | 41 wt % |

A sheet-type cosmetic pack was prepared in the same manner as in Example 1, using the cosmetic raw material substances with the film-forming property.

Comparative example 7

| | |
|---|---|
| Cation-based water-soluble copolymer (formula 1:H · C polymer 2, Osaka Organic Chem. Co. of Japan) | 20 wt % |
| Hydroxypropyl methylcellulose | 20 wt % |
| Polyacrylic acid | 5 wt % |
| Titanium oxide | 1 wt % |
| Silica (Aerosil 150) | 1 wt % |
| Polyethylenglycol | 2 wt % |
| Ethanol | 10 wt % |
| Lavender oil | 0.5 wt % |
| Distilled water | 40.5 wt % |

A sheet-type cosmetic pack was prepared in the same manner as in Example 1, using the cosmetic raw material substances with the film-forming property.

EXPERIMENTAL EXAMPLE

The physical properties of each sheet-type cosmetic pack, so obtained from the Examples and Comparative examples, were evaluated. The results of the evaluation are shown in the following table 1.

The removal rate of the keratotic plugs was calculated according to the following equation of evaluation:
Removal rate (number of keratotic plugs attached onto a 1 cm² pack)/of keratotic plugs (%)=(number of keratotic plugs on the skin of a nose)×100

○: over 25% removal of keratotic plugs
Δ: 5~20% removal of keratotic plugs
x: less than 5% of removal of keratotic plugs The strength and residue of the film was evaluated as follows:
○: strong with no residue
Δ: weak with slight amount of residue
x: weak with considerable amount of residue Pain at the time of a peel-off was evaluated as follows:
○: negligible pain
Δ: slight pain
x: considerable pain

TABLE 1

| Item | Removal Rate of keratotic plugs | Composition Strength | Composition Residue | Pain at the time of a peel-off |
|---|---|---|---|---|
| Example 1 | ○ | ○ | ○ | ○ |
| Example 2 | ○ | ○ | ○ | ○ |
| Example 3 | ○ | ○ | ○ | ○ |
| Example 4 | ○ | ○ | ○ | ○ |
| Example 5 | ○ | ○ | ○ | ○ |
| Example 6 | ○ | ○ | ○ | ○ |
| Example 7 | ○ | ○ | ○ | ○ |
| Comp. Exp. 1 | ○ | Δ | Δ | Δ |
| Comp. Exp. 2 | Δ | Δ | Δ | Δ |
| Comp. Exp. 3 | Δ | Δ | ○ | Δ |
| Comp. Exp. 4 | Δ | Δ | Δ | Δ |
| Comp. Exp. 5 | Δ | Δ | Δ | Δ |
| Comp. Exp. 6 | Δ | Δ | Δ | Δ |
| Comp. Exp. 7 | ○ | Δ | Δ | Δ |

As revealed in the results based on the Examples and Comparative examples, a cation-based water-soluble copolymer expressed by the formula 1 was added to the cosmetic raw material composition layer in order to effectively remove the keratotic plugs. Further, in order to remove the cosmetic residue on the skin of a nose, the strength of a film of the cosmetic composition layer was improved in such a manner that a water-soluble polymer or water-swelling polymer was partially cross-linked in the presence of a cross-linking agent to form an interpenetrating polymer network in the film of the cosmetic composition layer.

Consequently, the sheet-type cosmetic pack of this invention can prevent pain on the skin and remove dirt from the pores of the skin.

What is claimed is:

1. A cosmetic pack in the form of a sheet, the cosmetic pack comprising a protective film layer, a cosmetic raw material composition layer containing a cosmetic composition, and a substrate layer supporting the cosmetic composition, where said cosmetic raw material composition layer comprises a water-soluble polymer which is cross-linked in the range of 5–20% by a cross-linking agent and a cationic copolymer expressed by the following formula 1:

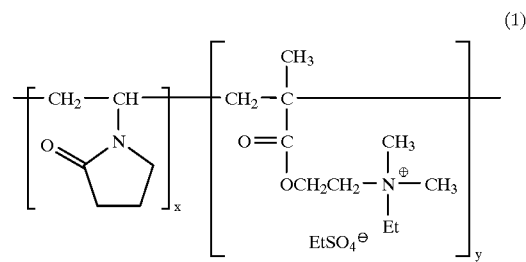

wherein, x is 0.6~0.8, y is 0.2~0.4, and x+y=1.

2. The cosmetic pack according to claim 1, wherein the total composition of the cosmetic raw material composition layer comprises 10~25 wt % of said cationic copolymer expressed by the above formula 1.

3. The cosmetic pack according to claim 1, wherein said water-soluble polymer is selected from the group consisting of hydroxypropylcellulose, hydroxypropylmethylcellulose, polyvinylpyrrolidone, polyvinyl alcohol, gelatin, methylcellulose, polyacrylic acid, polyethylene oxide, ethylcellulose and carboxylmethylcellulose.

4. The cosmetic pack according to claim 1 or 3, wherein the total composition of the cosmetic raw material composition layer comprises 30~55 wt % of said water-soluble polymer.

5. The cosmetic pack according to claim 4, wherein said water-soluble polymer comprises 3~20 wt % of a water-soluble polymer containing a hydroxy or carboxyl group.

6. The cosmetic pack according to claim 1, wherein said cross-linking agent is selected from the group consisting of calcium chloride, aluminum sulfate, polyethylene glycolglysidyl ether and triglycerine diglysidyl ether.

7. The cosmetic pack according to claim 1 or 6, wherein the total composition of the cosmetic raw material composition layer comprises 2~7 wt % of said cross-linking agent.

8. The cosmetic pack according to claim 1, wherein the total composition of the cosmetic raw material composition layer comprises 1~3 wt % of silica powder.

9. The cosmetic pack according to claim 1, wherein said cosmetic composition raw material layer comprises commonly available cosmetic additives which include the ingredients for moisture retention, perfume, and pore reduction.

* * * * *